United States Patent [19]

Mura

[11] Patent Number: 5,760,227

[45] Date of Patent: Jun. 2, 1998

[54] COMPOUNDS OF THE S-TRIAZINE SERIES

[75] Inventor: Jean-Luc Mura, Rixheim, France

[73] Assignee: Clariant Finance (BVI) Limited, Tortola, Virgin Islands (Br.)

[21] Appl. No.: 690,695

[22] Filed: Jul. 31, 1996

Related U.S. Application Data

[63] Continuation of Ser. No. 408,506, Mar. 22, 1995, abandoned.

[30] Foreign Application Priority Data

Mar. 24, 1994 [DE] Germany .................. 44 10 115.5

[51] Int. Cl.⁶ .................................................. C07D 251/50
[52] U.S. Cl. .................. 544/208; 544/194; 544/204; 544/211; 544/213; 544/217; 544/218
[58] Field of Search .................. 544/194, 204, 544/208, 211, 213, 217, 218

[56] References Cited

U.S. PATENT DOCUMENTS

| | | | |
|---|---|---|---|
| 1,625,531 | 4/1927 | Fritzsche et al. | 544/194 |
| 1,625,532 | 4/1927 | Fritzsche et al. | 544/194 |
| 3,689,487 | 9/1972 | Mason et al. | 260/249.8 |
| 3,907,698 | 9/1975 | Loffelman et al. | 252/99 |

FOREIGN PATENT DOCUMENTS

| | | |
|---|---|---|
| 0 053 775 | 6/1982 | European Pat. Off. |
| 0 072 009 | 2/1983 | European Pat. Off. |
| 0 165 608 | 12/1985 | European Pat. Off. |
| 0 245 204 | 11/1987 | European Pat. Off. |
| 0 252 508 | 1/1988 | European Pat. Off. |
| 0252508 | 1/1988 | European Pat. Off. |
| 0 300 753 | 1/1989 | European Pat. Off. |
| 0 417 040 | 3/1991 | European Pat. Off. |
| 0 475 367 | 3/1992 | European Pat. Off. |
| 0 630 947 | 12/1994 | European Pat. Off. |
| 2167130 | 8/1973 | France . |
| 2 256 919 | 1/1975 | France . |
| 2 363 133 | 3/1978 | France . |
| 21 64 800 | 7/1973 | Germany . |
| 26 36 144 | 6/1977 | Germany . |
| 2917359 | 11/1980 | Germany . |
| 51050325 | of 1976 | Japan . |
| 51053083 | of 1976 | Japan . |
| 603 606 | 8/1978 | Switzerland . |
| 1247186 | 9/1971 | United Kingdom . |
| 1318217 | 5/1973 | United Kingdom . |
| 1496635 | 12/1977 | United Kingdom . |
| 2 011 883 | 7/1979 | United Kingdom . |
| 2 119 367 | 11/1983 | United Kingdom . |
| WO 86 03528 | 6/1986 | WIPO . |

OTHER PUBLICATIONS

Journal of Heterocyclic Chemistry, Lowe et al., vol. 13, 1976, pp. 829–833.

"The Chemistry of Synthetic Dyes", K. Venkataraman, vol. V, Academic Press, New York & London, 1971, pp. 538–543 & 573.

C.A. 100: 105050, 1984.

C.A. 98:55536, 1983 (Hanguk).

C.A. 97: 199537, 1982 (Norek).

*Primary Examiner*—Yogendra N. Gupta
*Attorney, Agent, or Firm*—Hesna J. Pfeiffer

[57] ABSTRACT

The compounds of the s-triazine series of formula I wherein the symbols $R_1$, $R_2$, $R_3$, X and n possess the significances given in claim 1, are eminently suitable, when applied to textile material, as UV-absorbers, as resist agents for anionic dyes, and as stain blockers.

4 Claims, No Drawings

COMPOUNDS OF THE S-TRIAZINE SERIES

This is a continuation of application Ser. No. 08/408,506, filed Mar. 22, 1995, now abandoned.

The invention relates to compounds of the s-triazine series, which are eminently suitable as UV-absorbers when applied in the field of textiles, and which in addition bestow stain-blocking properties on the textile material treated therewith. In addition, the places on the textile material that have been treated with the new compounds show a resist action towards anonic dyes.

The new compounds correspond to formula I

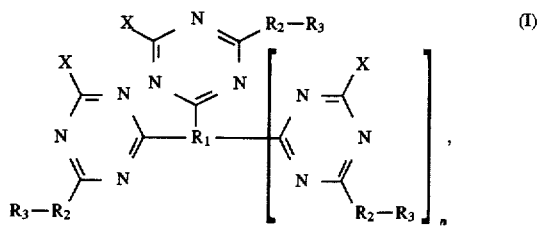

wherein $R_1$ when n=0, signifies the radical of an aromatic, cycloaliphatic, heterocyclic diamine or diamide which optionally bears 1 or 2 further substituents, or the radical of a $C_{1-22}$-aliphatic diamine or diamide which optionally bears 1 or 2 substituents and/or is interrupted by hetero atoms, or when n=1, signifies the radical of an aromatic, $C_{3-12}$-aliphatic or cycloaliphatic triamine or triamide, each $R_2$ independently signifies a —NH—, —O—, —S—, —*NHCO— or —*OCO— bridge, where * signifies an atom bonded to the triazine ring, each $R_3$ independently signifies a $C_{1-12}$-aliphatic, cycloaliphatic, mono- or binuclear, aromatic or heterocyclic radical, wherein these radicals may bear one or two substituents, each X independently signifies fluorine, chlorine or bromine, and n signifies 0 or 1, with the proviso that each compound carries at least one water-solubilizing group.

The said aromatic radicals are phenyl or naphthyl radicals, especially phenyl radicals. The cycloaliphatic radicals preferably contain 5 or in particular 6 carbon atoms. The heterocyclic radicals may be saturated, partly unsaturated and also those of aromatic character. The aromatic diamines ($R_1$) may be, for example, o-, m- or p-phenylenediamine, preferably p-phenylenediamine, but also 2,5-diaminothiophene.

The substituents on the radicals of aromatic character may be in particular halogen atoms, preferably chlorine or bromine, or methyl, hydroxyl, $C_{1-2}$-alkoxy, carboxy, alkoxycarbonyl or sulphonic acid groups. Substituents on the radicals of aliphatic character may be e.g. hydroxyl, $C_{1-4}$-alkoxy, carboxy, $C_{1-3}$-alkoxycarbonyl or $C_{1-3}$-alkylcarbonyloxy groups.

Preferred diamide radicals are e.g. o-, iso- or terephthalic acid diamide radicals, 2,5-thiophene-dicarboxylic acid diamide radicals or $C_{2-12}$-alkylene-dicarboxylic acid diamidle radicals.

Triamide radicals which may be used include trimesic acid triamide, trimellitic acid triamide or citric acid triamide radicals.

The following significances preferably respectively apply and are independent of one another in every respect, $R_1$ signifies a phenylenediamine radical which optionally bears one or two substituents from the series chlorine, bromine, methyl or $C_{1-2}$-alkoxy, each $R_2$ signifies a —NH— bridge, each $R_3$ signifies a phenyl radical which optionally bears one or two sulphonic acid groups, each X signifies fluorine or chlorine, and n=0.

Production of the new compounds of formula I is effected by the condensation of 2+n mols of a compound or mixture of compounds of formula II

with 1 mol of a compound of formula III

and 2+n mols of a compound or mixture of compounds of formula IV

The condensation reactions of compounds of formulae III and IV with trihalogen-s-triazines are familiar to the person skilled in the art and do not need to be described more fully here.

These new compounds are reactive towards textile materials containing hydroxyl or amino groups (untreated or regenerated cellulosic materials, natural and synthetic polyamides), which means that the materials containing hydroxyl or amino groups, which are treated with these compounds according to the invention, are finished in such a way that they permanently absorb UV-rays and are stain-blocking and useful as resist agents for anionic dyes. When wearing textiles that have been finished in this way, the skin underneath the textiles is very efficiently protected against aggressive UV radiation.

The new compounds of formula I mainly absorb UVB and UVC radiation, but hardly any UVA radiation, so that they practically do not affect the action of optical brighteners.

The new compounds are generally applied to the said substrates in the same way as the known reactive dyes, optionally together with such dyes, and are preferably fixed by applying heat. The procedure may be carried out according to known exhaust processes or a padding/slop-padding process or a known printing process.

In general, 0.05 to 5%, preferably 0.1 to 3%, especially 0.5 to 2.5% of one or more compounds of formula I is used, based on the weight of the substrate. These new compounds are absorbed very well by the said substrates. In addition, the surfaces of textiles that have been dyed or printed by them can later only be dyed poorly or not at all by anionic dyes. If it is desired that the subsequent dyeability should be substantially reduced, then preferably more than 2.5%, e.g. 3 to 8%, of the new compounds of formula I, is used, based on the weight of the substrate treated. The usage as a resist agent takes place analogously to the processes described in GB Patent Specification 2 011 883.

In the following examples, the parts and percentages are by weight. 1 part by volume corresponds to 1 part by weight of water (at +4° C.). The temperatures are given in degrees celsius.

Example 1

50 parts of trichiorotriazine is stirred into 400 parts of water at 0°–5°, then after ca. 15 minutes mixed with 48 parts of sulphanilic acid, and the mixture is stirred for a further ca. 90 minutes. The resultant hydrochloric acid is neutralized by gradually adding 54 parts by volume of 30% sodium hydroxide solution. Afterwards, 15.4 parts of m-phenylenediamine is introduced whilst stirring, the reaction mixture is heated to 50°, the pH value thereof is maintained at 7 by adding approximately 20% soda solution, the resultant suspension is filtered off (e.g. through a suction filter) and the filter cake is dried at 50°. The di-sodium salt of the compound of formula of Glauber's salt. 1 part of the compound obtained according to example 1 is then added, the substrate is agitated in the bath for 15 minutes, 10 parts of soda is added, the bath is heated to 80° over 20 minutes, and the substrate is treated at this temperature for a further 30 minutes. The cotton fabric is then removed from the bath, given firstly a hot rinse, then a cold rinse, and dried.

The compounds produced according to examples 2 to 8 may also be applied to cotton fabric in the same way. The fixing yields, determined by means of spectrophotometric

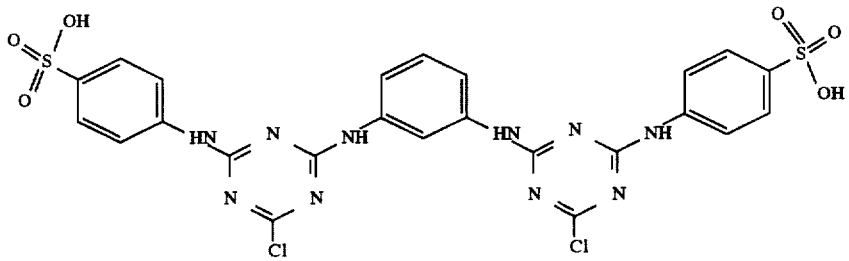

is thus obtained.

In the following table further compounds according to the invention, of formula measurement of the content of UV-absorber in the bath (before and after treatment of the substrate), are as follows:

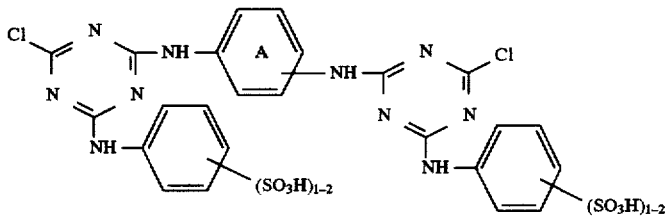

are listed, which may be produced analogously to the procedure of the 1st example.

TABLE

| Ex. No. | bonding to ring A | position of —SO$_3$H |
|---|---|---|
| 2 | para | 4' |
| 3 | ortho | 4' |
| 4 | para | 2' and 5' |
| 5 | para | 3' |
| 6 | ortho | 2' and 5' |

Examples 7 and 8

The process is as given in example 1, but the 15.4 parts of m-phenylenediamine is replaced by 8.55 parts of ethylenediamine (ex. 7) or 10.5 parts of 1,3-diaminopropane (ex. 8), and compounds of formula I are obtained, wherein $R_1$ signifies the divalent residue of 1,2-ethylenediamine resp. 1,3-propylenediamine, the two $R_2$ signify —NH—, the two $R_3$ signify p-phenylene-para-sulphonic acid, X=chlorine and n=0.

Application as a UV-absorber. Application Examples 1–6

Application Example 1

100 parts of cotton fabric is placed in 1000 parts of an aqueous liquor, which is heated to 60° and contains 80 parts

| Compound according to example | Fixing yield |
|---|---|
| 1 | 86% |
| 2 | 73% |
| 3 | 46% |
| 4 | 75% |
| 5 | 77% |
| 6 | 30% |
| 7 | 42% |
| 8 | 42% |

The textile materials thus obtained are very efficiently protected against damage from light, and, in comparison with material that has not been treated according to the invention, have better stain-blocking action, and their dyeability with anionic dyes is reduced. Their light transmission to UVB- and UVC-rays is so low that these textiles offer the wearer effective protection against UVB- and UVC-radiation.

Application Examples 2–5

100 parts of cotton jersey (200 g/m$^2$) as well as X parts of compound of example 1 are placed in 1000 parts of an aqueous liquor, which contains 80 parts of Glauber's salt. The bath is then headed to 95° over 30 minutes, 10 parts of soda is added and the substrate is treated at this temperature for 30 minutes. The cotton fabric is then removed from the bath, given firstly a hot rinse, then a cold rinse, and dried.

Transmission measurements are then carried out, und the sun protection factor (UPF, ultraviolet protection factor, according to the Australian Radiation Laboratory) is calculated.

| Application Example | Parts of Compound of Exp. 1 | UPF |
|---|---|---|
| 2 | 0 | 5 |
| 3 | 0.16 | 20 |
| 4 | 0.48 | 25 |
| 5 | 0.8 | 30 |

Application Example 6

100 parts of polyamide 66 (nylon fabric, 130 g/m$^2$) as well as 0.24 parts of the compound of example 1 are placed in 1000 parts of an aqueous liquor which contains 80 parts of Glauber's salt. This liquor is heated to 95° over 30 minutes and kept for 45 minutes at this temperature. After the cooling the fabric is removed from the bath, given a hot and cold rinse and dried. The sun protection factor (UPF) is increased from 10 to 20 by such a treatment.

Application as a stain-blocker. Application Examples 7 and 8

Application Example 7

100 parts of wool fabric is treated for 60 minutes at 95° C. and pH 4 with 5 parts of the compound as obtained in example 1 (ratio of goods to liquor 1:19). After cooling to 70° C. 5 parts of a formaldehyde condensation product of naphthalenesulphonic acid and dihydroxydiphenylsulfone is added and treatment is continued for another 20 minutes. The fabric treated in this manner shows excellent protection in the staining test with C.I. Food Red 17 (IWS draft test method No. 282).

Application Example 8

100 parts of polyamide 6.6 is treated in the same manner as the 100 parts of wool fabric in application example 7. The fabric treated in this manner shows excellent protection in the staining with C.I. Food Red 16.

Application Example 9 (as resist agent)

A pattern is printed on to 100 parts of polyamide 6.6 at pH 6.5 with a paste which contains 2.5 parts of the compound as obtained in example 1, 2.0 parts of salt and a thickener based on alginate (pick up 100%). Thereafter the pattern is fixed for 20 minutes in saturated steam at 102° C. After thorough rinsing the fabric is dyed for one hour at 98° C. in a bath which contains 0.55 parts C.I. Acid Red 57 and 0.45 parts C.I. Acid Red 266 at a good to liquor ratio of 1:10. After dyeing and rinsing a pattern is obtained which shows patches which are lighter than the dyed background where the fabric was preprinted.

I claim:

1. The compounds of the general formula IA

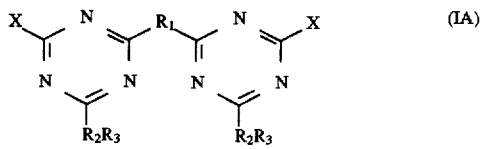

wherein $R_1$ is phenylene diamine or ethylene diamine, optionally substituted with 1–2 substituents chlorine, bromine, methyl, or $C_{1-2}$alkoxy;

X is fluorine or chlorine;

$R_2$ is an amino bridge; and $R_3$ is phenylene substituted with 1 or 2 sulfonic acid groups.

2. The compounds of claim 1 in which $R_1$ is phenylene diamine;

X is chlorine;

$R_2$ is an amino bridge; and $R_3$ is phenylene substituted with 1 or 2 sulfonic acid groups.

3. The compounds of claim 2 in which $R_3$ is phenylene substituted with 1 sulfonic acid group.

4. The compounds of claim 3 in which the sulfonic acid group is para.

* * * * *